(12) United States Patent
Asai et al.

(10) Patent No.: US 8,052,856 B2
(45) Date of Patent: Nov. 8, 2011

(54) SUPPORT FOR CAPILLARIES, CASE FOR CONSTRAINING CAPILLARIES INCLUDING THE SAME

(75) Inventors: Masao Asai, Shiga (JP); Masahiro Okumura, Shiga (JP); Yoshihiro Okawa, Shiga (JP)

(73) Assignee: Kyocera Corporation, Kyoto (JP)

( * ) Notice: Subject to any disclaimer, the term of this patent is extended or adjusted under 35 U.S.C. 154(b) by 990 days.

(21) Appl. No.: 11/963,778

(22) Filed: Dec. 21, 2007

(65) Prior Publication Data

US 2008/0171178 A1 Jul. 17, 2008

(30) Foreign Application Priority Data

Dec. 26, 2006 (JP) .................................. 2006-350676
Mar. 27, 2007 (JP) .................................. 2007-080787

(51) Int. Cl.
*G01N 27/453* (2006.01)
(52) U.S. Cl. ........................................ 204/601; 204/452

(58) Field of Classification Search .......... 204/601–640, 204/451–553
See application file for complete search history.

(56) References Cited

U.S. PATENT DOCUMENTS

| 7,067,085 B1 * | 6/2006 | Sugawara et al. ............. 264/676 |
| 2002/0003091 A1 * | 1/2002 | Kojima et al. ................ 204/603 |

FOREIGN PATENT DOCUMENTS

| JP | 2001-019540 A | 1/2001 |
| JP | 2001-302341 A | 10/2001 |
| JP | 2002-167267 A | 6/2002 |
| JP | 2003-315308 A | 11/2003 |

* cited by examiner

*Primary Examiner* — Jeffrey T Barton
*Assistant Examiner* — J. Christopher Ball
(74) *Attorney, Agent, or Firm* — Birch, Stewart, Kolasch & Birch, LLP

(57) ABSTRACT

A support for capillaries comprises a ceramic member having a flat surface area on which the capillaries are to be aligned. The flat surface area has a flatness of not more than 0.02 mm and has a mean spacing of waviness motifs (AW) of not more than 100 μm.

10 Claims, 9 Drawing Sheets

SUPPORT FOR CAPILLARIES, CASE FOR CONSTRAINING CAPILLARIES INCLUDING THE SAME

CROSS-REFERENCE TO RELATED APPLICATIONS

The present application claims priority of Japanese Patent Applications No. 2006-350676, filed on Dec. 26, 2006, and No. 2007-080787, filed on Mar. 27, 2007. The contents of these applications are incorporated herein by reference in their entirety.

FIELD OF THE INVENTION

The present invention relates to a support for capillaries, and a case for constraining the capillaries including the support which can be used for an electrophoresis apparatus for detecting and measuring the components such as DNA and RNA.

DESCRIPTION OF THE RELATED ART

Analysis techniques of deoxyribonucleic acids (DNAs) and ribonucleic acids (RNAs) have become important in the performance of gene analysis and genetic diagnosis. Therefore, DNA analyzers for performing gene analysis at high speeds have been developed. For example, DNA analysis is performed by electrophoresing samples for analysis charged in a plurality of capillaries to separate a plurality of types of molecules in the samples utilizing the difference in their molecular weights, irradiating a laser beam so as to cross over the capillaries, and detecting and analyzing fluorescence emitted by the irradiation of the laser beam.

Japanese Unexamined Patent Application Publication No. 2003-315308 (document '308) discloses a capillary electrophoresis apparatus for gene analysis. In the capillary electrophoresis apparatus, a fluorinated polymer is filled in a capillary-fixing container (support for capillaries) to cover at least half of the external surfaces of the cross sections of a plurality of capillaries or the entire surfaces thereof. The capillary electrophoresis apparatus includes a capillary array in which the optical path of a laser beam crosses over in the direction parallel to the plurality of capillaries. The support for capillaries used in the capillary electrophoresis apparatus disclosed in document '308 is made of quartz glass.

When a support for capillaries is made of quartz glass as in the electrophoresis apparatus disclosed in document '308, a laser beam is transmitted from the support for capillaries as scattered light because of the transparency of the quartz glass, thus making DNA analysis difficult.

Therefore, the use of black quartz glass produced by blackening quartz glass as a support for capillaries has been studied.

Black quartz glass is produced by, for example, mixing heavy metal oxides with a natural quartz glass powder, and fusing the mixture. Therefore, the heavy metal is inhomogeneously contained in the resulting glass. As a result, such black quartz glass includes a large number of areas having a pale color (color heterogeneity) on the surface thereof. Accordingly, when capillaries are disposed on a support for capillaries made of black quartz glass and are irradiated with a laser beam, a part of the laser beam is easily reflected at the areas of the support having such a pale color. As a result, the laser beam may be transmitted and emitted from the support for capillaries as scattered light.

Consequently, in order to reduce this reflection of a laser beam, instead of black quartz, studies of using ceramic as a support for capillaries have been performed.

However, when a ceramic sinter is used as a support for capillaries, and, for example, 96 capillaries are aligned in the support for capillaries to be adjacent to each other, the positions of the capillaries are varied in the vertical direction of the support surface because of concave and convex portions formed on the surface of the ceramic sintered body. Consequently, when a laser beam is irradiated to cross over the capillaries, the laser beam is significantly refracted at a position halfway through the aligned capillaries, and the optical path of the laser beam becomes deflected from the center of the capillaries, thus causing a decrease in the measurement accuracy. In particular, when capillaries having a small outer diameter in the range of 0.2 to 2 mm are used, the effect of displacement of the capillaries in the vertical direction on the analysis accuracy is increased. Therefore, a support for capillaries in which the displacement and positional variation of capillaries in the vertical direction can be decreased has been strongly desired.

DESCRIPTION OF THE PREFERRED EMBODIMENTS

According to one aspect of the invention, a support for capillaries comprises a ceramic member having a flat surface area on which the capillaries are to be aligned. The flat surface area has a flatness of not more than 0.02 mm and has a mean spacing of waviness motifs of not more than 100 μm.

According to another aspect of the invention, the support for capillaries comprises a ceramic member having a flat surface area on which the capillaries are to be aligned. The flat surface area has a flatness of not more than 0.02 mm and has a mean spacing of waviness motifs of not more than 100 μm.

A support for capillaries and a case for capillaries according to an embodiment of the present invention will now be described in detail. In the embodiment, the support for capillaries and the case for capillaries are described in detail using, as an example, a capillary array structure 100 included in an electrophoresis apparatus used for measuring or identifying a measurement sample (e.g., component contained in an organism (such as a DNA, an RNA, or a protein)).

Overall Configuration of Capillary Array Structure

Figure 1A:
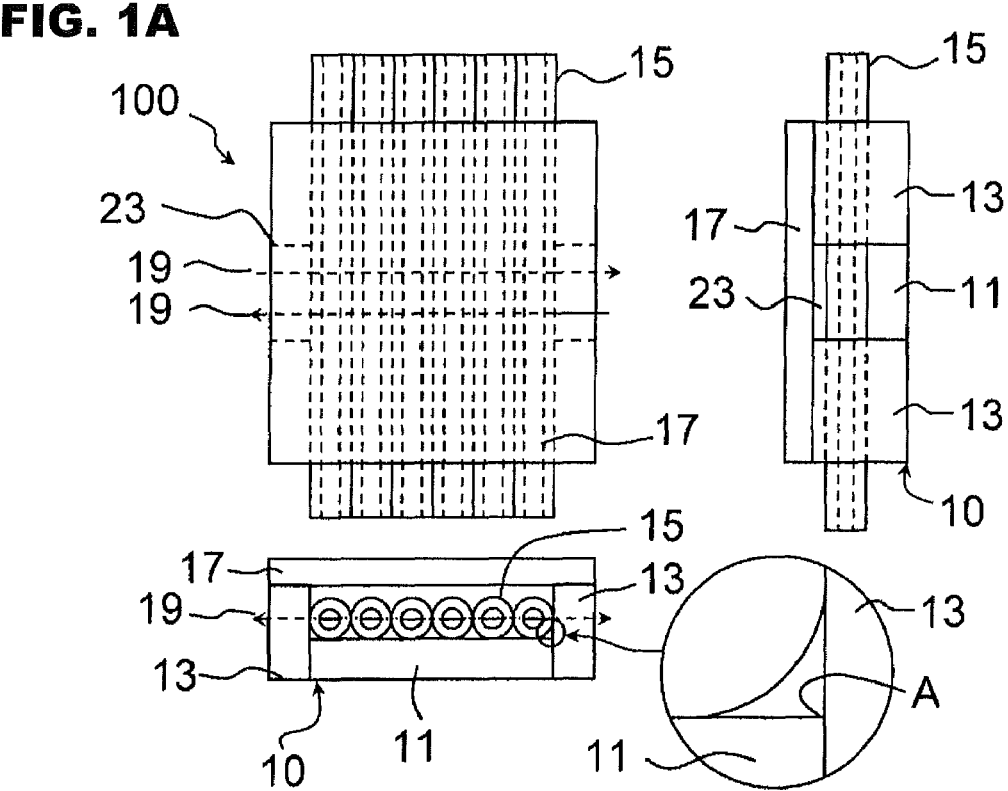
FIG. 1A illustrates both a plan view and a side view of a capillary array structure having a case having a support in accordance with an embodiment of the invention.

As shown in FIG. 1A, the capillary array structure 100 according to the embodiment includes a capillary array in which a plurality of capillaries 15 each of which is filled with an electrophoretic medium containing a measurement sample are aligned, and a case 10 for capillaries that accommodates the capillary array.

Figure 2:
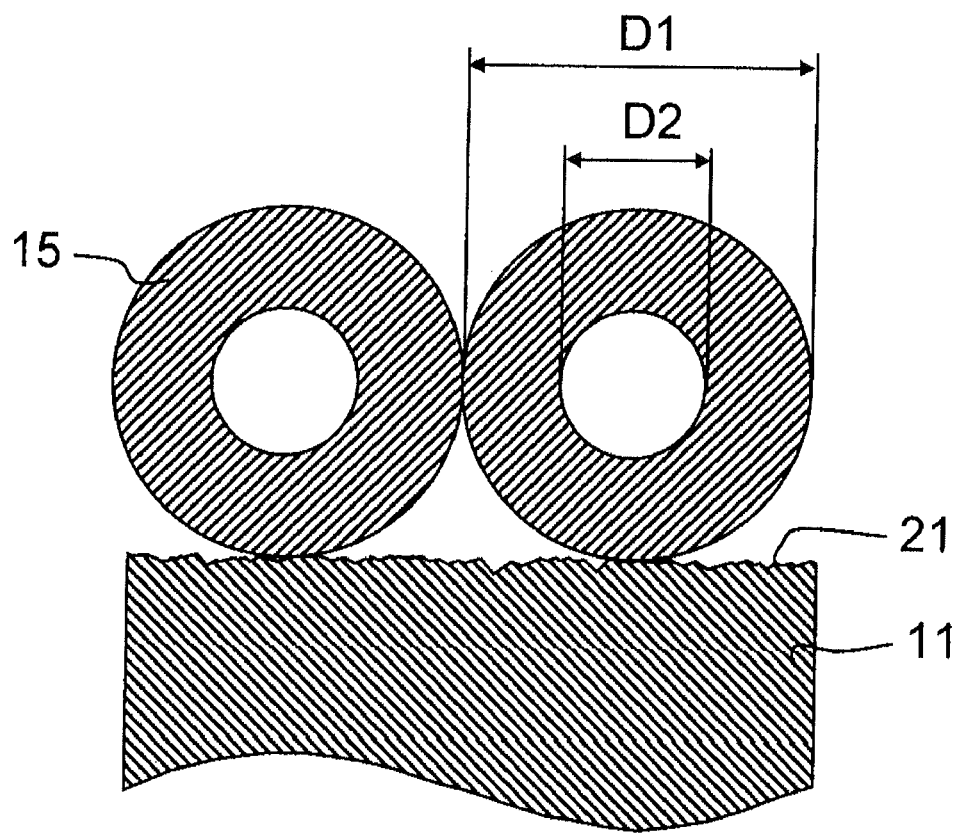
FIG. 2 illustrates a partial enlarged view of the configuration where the capillaries are disposed on the support.

Each of the capillaries 15 is typically composed of quartz glass and has a cylindrical shape. In general, the outer diameter D1 of each capillary is determined in the range of 0.2 to 0.4 mm, and the inner diameter D2 thereof is determined in the range of 0.05 to 0.15 mm. In addition, as shown in FIG. 2, adjacent capillaries 15 are in contact with each other. As a material of capillaries 15, the optically-transparent material other than quartz glass may be used.

The case 10 for capillaries includes a support 11 for capillaries that supports the capillary array, side walls 13 disposed at both sides of the support 11 for capillaries, and a lid 17 disposed on the side walls 13.

In the measurement of a measurement sample using this capillary array structure 100, an electrophoretic medium containing the measurement sample is supplied in the capillaries 15, and the electrophoretic medium is electrophoresed by applying a voltage to the electrophoretic medium. A laser beam is then irradiated onto the capillary array from a direction orthogonal to the longitudinal direction of the capillaries 15. Components in the measurement sample are detected by observing fluorescence emitted from the electrophoretic medium by the irradiation of the laser beam.

Configuration of Case for Capillaries

The support 11 for capillaries included in the case 10 for capillaries is composed of a ceramic member and includes a flat surface area 21 on which a plurality of capillaries 15 are aligned. The flatness of the flat surface area 21 is determined so as to be not more than 0.02 mm (preferably not more than 0.01 mm), and the mean spacing of waviness motifs (AW) in the flat surface area 21 is determined so as to be not more than 100 μm (preferably not more than 50 μm).

In the embodiment, this support 11 for capillaries comprises a black ceramic having low black heterogeneity. Therefore, even if light leaks from a laser beam irradiated into the capillaries 15 and the support 11 for capillaries is irradiated with the leaked light, the irradiated light is successfully absorbed by the support 11 for capillaries. Consequently, the reflection of the laser beam by the support 11 for capillaries is effectively reduced to improve the performance of the capillary array structure 100.

Note that as ceramic materials of the support 11, any ceramics other than black ceramic may be used. Preferably, the support 11 comprises the ceramics having a property of not more than 30% of the optical reflectance to the laser beam irradiated into the capillaries 15 to improve the performance of the capillary array structure 100. Generally, the darker the color of the support 11, the lower reflectance to light the support 11 has. Since the black ceramic can make it easier to allow the support 11 to have the low optical reflectance of the above range, the support 11 comprising the black ceramic is preferable.

The support 11 for capillaries is preferably made of a material having a thermal expansion coefficient close to that of the capillaries 15. When the capillaries are made of quartz, in particular, the support 11 for capillaries is preferably made of a material containing cordierite as a primary component.

A pair of side walls 13 that can constrain the capillaries 15 in the width direction thereof (in the direction orthogonal the longitudinal direction of the capillaries 15) are disposed at both sides of the support 11 for capillaries.

Each of the side walls 13 includes an opening 23 for transmitting laser beams 19. When the laser beams 19 enter from the opening 23, the laser beams 19 are transmitted through the measurement sample in the capillaries 15. For example, an argon laser beam is used as each of the laser beams 19 and is irradiated from both sides of the capillary array. The laser beams 19 are transmitted through the capillaries 15 without intersecting each other.

The lid 17 is disposed on the side walls 13. The capillaries 15 are aligned in a space surrounded by the support 11 for capillaries, the side walls 13, and the lid 17. All of or a part of the space is filled with a resin material (not shown) such as a fluorinated polymer. This resin material has functions of fixing the capillaries 15 and effectively reducing the reflection of the laser beams 19 at the interface between the capillaries 15 and the resin material. A resin having a refractive index close to that of the capillaries 15 is preferably used as the resin material.

In the embodiment, the curvature radius of a corner at a boundary A between the side walls 13 and the flat surface area 21 is determined so as to be not more than the curvature radius of the capillary 15. This structure can successfully reduce contact of the boundary A with a capillary 15, decrease the variation in vertical positions of the plurality of capillaries 15, and allow the laser beams 19 to be irradiated into the capillaries 15 with a high accuracy. As shown in FIG. 1A, at the corner of the boundary A, the flat surface area 21 and the side walls 13 are preferably disposed to be orthogonal to each other. When the flat surface area 21 and each of the side walls 13 are disposed to be orthogonal to each other, the support 11 for capillaries and the side walls 13 can be integrated by joining these components to each other. Accordingly, the capillary array structure 100 can be easily produced.

The side walls 13 and the lid 17 are preferably made of the same ceramic material as the support 11 for capillaries. Like the support 11, the side walls 13 and/or lid 17 preferably comprises the ceramics having a property of not more than 30% of the optical reflectance to the laser beam irradiated into the capillaries. The black ceramic is more preferable to make it easier to allow the side walls 13 and/or lid 17 to have the low optical reflectance of the above range.

Flatness and Mean Spacing of Waviness Motifs of Support 11 for Capillaries

Figure 3A:
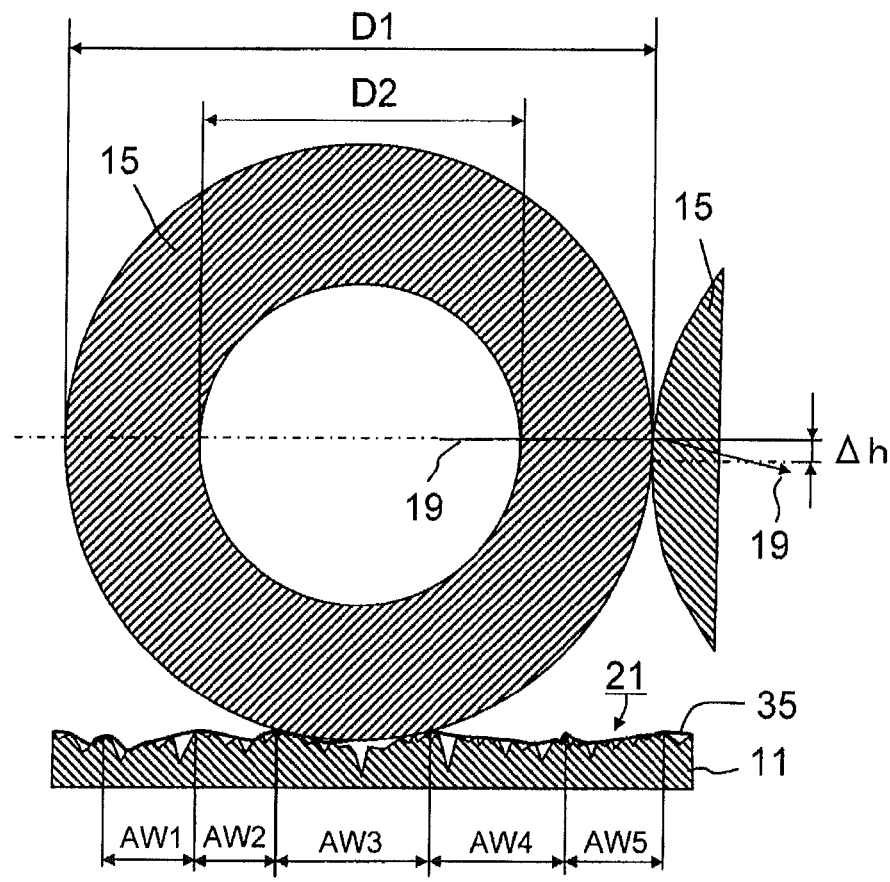
FIG. 3A illustrates a partial enlarged cross-sectional view of a flat surface area of the support and the capillaries aligned on the flat surface area.
Figure 3B:
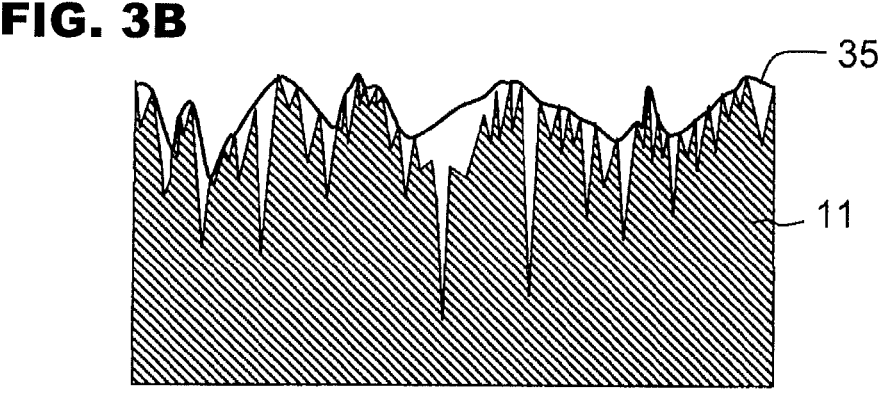
FIG. 3B illustrates a partial enlarged cross-sectional view of the surface of the support in FIG. 3A.

The flatness and waviness motifs of the flat surface area 21 of the above-described support 11 for capillaries will now be described in detail with reference to FIGS. 3A and 3B.

The reasons that the flatness of the flat surface area 21 is determined to be not more than 0.02 μm and that the mean spacing of waviness motifs (AW) is determined to be not more than 100 μm are considered to be as follows.

In the detection of components in a measurement sample using the capillary array structure 100, first, a laser beam 19 is irradiated onto the central positions of the capillaries 15. If the central positions of the cross section of the capillaries 15 are misaligned, the laser beam 19 is refracted, and the optical path of the laser beam 19 is shifted from desired positions. Therefore, the vertical positions of the center of the capillaries 15 are preferably aligned as much as possible. According to the result of an experiment, when the flatness of the flat surface area 21 is controlled to be not more than 0.02 mm, the variation in the vertical positions of the center of the capillaries 15 aligned on the flat surface area 21 can be reduced to some extent, but the central positions of the cross section of the capillaries 15 are still varied. That is, in order to effectively improve the measurement accuracy or the like of the capillary array structure 100, a countermeasure other than a decrease in the surface roughness of the flat surface area 21 is necessary. According to the result of an examination made by the inventors, the variation in the vertical positions among the capillaries 15 is mainly generated because the capillaries 15 are fitted in a large number of valleys formed on the surface of the support 11 for capillaries, as shown in FIG. 3A. It is believed that these valleys are formed because ceramic particles in the ceramic constituting the support 11 for capillaries become partly detached from the support 11 or pores are present in the ceramic. In FIG. 3A, the amount of shift in the central positions of adjacent capillaries 15 in the vertical direction is represented by Δh. As the amount of shift Δh increases, the angle in which the laser beam 19 is refracted at the interface of adjacent capillaries 15 also increases. As a result, the optical path of the laser beam 19 is easily shifted from desired positions. In particular, in an outer diameter of the capillaries 15 of not more than 0.3 mm, it is more important that the vertical positions of the center of the capillaries 15 be aligned as much as possible.

As a result of studies conducted by the inventors, it has been found that when the mean spacing of waviness motifs (AW) of the flat surface area 21 is determined so as to be not more than 100 μm, the shift in the central positions of the cross section of the capillaries 15 can be reduced, the refraction of the laser beam 19 can be reduced, thus reducing the shift in the optical path of the laser beam 19. The reason why such advantages can be achieved is considered to be as follows: As shown in FIG. 3B, when an imaginary envelope waviness curve 35 is drawn on the surface of the flat surface area 21, a capillary 15 is easily located in a state in which it is in contact with tops of the envelope waviness curve 35. Accordingly, it is believed that if the spacing of waviness motifs (AW), which corresponds to the distance between two tops, is decreased, the degree that the capillary 15 is embedded in valleys can be decreased. The outer diameter of the capillaries 15 is generally in the range of about 0.2 to 2 mm. Accordingly, a mean spacing of waviness motifs (AW) of not more than 100 μm can satisfactorily contribute to an improvement in the performance of the capillary array structure 100.

Note that the flat surface area 21 has at least apart thereof where the conditions that the flatness is not more than 0.02 μm and the mean spacing of waviness motifs (AW) is not more than 100 μm are satisfied. Preferably, the part of the flat surface area 21 is not less than 50% of the flat surfaces area 21. More preferably, the entire of flat surfaces area 21 is satisfied with the conditions.

In addition, when the lower limit of the flatness of the flat surface area 21 is determined to be 0.001 mm and the lower limit of the mean spacing of waviness motifs (AW) is determined to be 10 μm, the labor and time required for forming a mirrored surface of the flat surface area 21 can be reduced.

The flatness of the flat surface area 21 can be measured using, for example, a three-point gauge. The mean spacing of waviness motifs (AW) of the flat surface area 21 can be measured using a surface roughness tester on the basis of ISO 12085: 1996 (Geometrical Product Specifications (GPS)-Surface texture: Profile method-Motif parameters) or Japanese Industrial standard (JIS) B0631 (2000), herein incorporated by reference.

Skewness (Rsk) of Support 11 for Capillaries

Figure 4A:
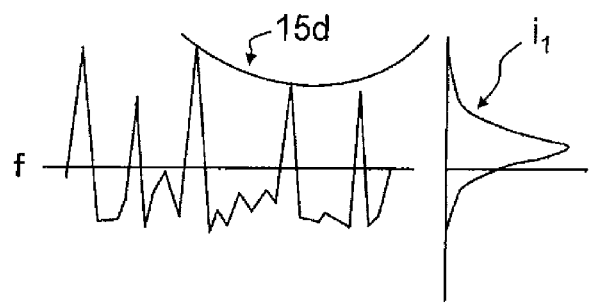
FIG. 4A illustrates a shaped curve line measured by surface roughness tester and amplitude distribution curve line in case of more than 0 of a skewness (Rsk).
Figure 4B:
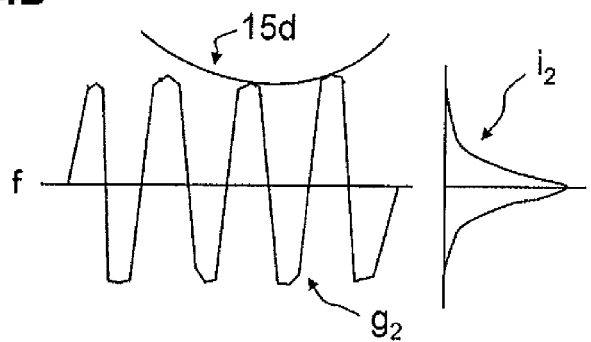
FIG. 4B illustrates a shaped curve line measured by surface roughness tester and amplitude distribution curve line in case of 0 of a skewness (Rsk).
Figure 4C:
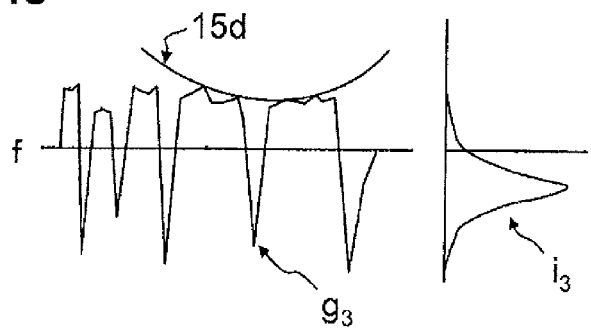
FIG. 4C illustrates a shaped curve line measured by surface roughness tester and amplitude distribution curve line in case of less than 0 of a skewness (Rsk).

The flat surface area 21 of the support 11 for capillaries preferably has a skewness (Rsk) of not more than zero. FIGS. 4A, 4B, and 4C are schematic diagrams showing curves ($g_1$, $g_2$, and $g_3$) measured with a surface roughness tester and distribution curves of amplitude ($i_1$, $i_2$, and $i_3$), respectively, illustrating the skewness (Rsk). In FIGS. 4A to 4C, a part of the circumference of a capillary 15 fixed on the flat surface area 21 is shown by an arc 15d. The skewness (Rsk), which is a parameter of the surface roughness, represents the degree of deviation in the vertical direction of the distribution curve of amplitude. The skewness (Rsk) is calculated using the following formula:

$$Rsk = \frac{1}{nRq^3} \sum_{i=1}^{n} (yi)^3$$

wherein n represents the number of ordinates on a curve measured with a surface roughness tester, Rq represents the mean square roughness (square root of the mean square of total deference between the curves and the average line f at every measured point within the measured length), and yi represents the height of the ordinate. More specifically, as shown in FIG. 4A, when the curve $g_1$ of the flat surface area 21 has a large number of sharp convex portions at positions located above the average line f, the distribution curves of amplitude $i_1$ becomes shifted to the upper side. Accordingly, the skewness (Rsk) is a positive value (>0). As shown in FIG. 4B, when the curve $g_2$ of the flat surface area 21 is located so that parts of the curve $g_2$ above and below the average line f are substantially equivalent and uniform in size in the vertical direction, the distribution curves of amplitude $i_2$ is shifted neither in the upper direction nor in the lower direction. Accordingly, the skewness (Rsk) is zero (=0). As shown in FIG. 4C, when the curve $g_3$ of the flat surface area 21 has a large number of sharp concave portions at positions located below the average line f, the distribution curves of amplitude $i_3$ becomes shifted to the lower side. Accordingly, the skewness (Rsk) is a negative value (<0).

When the skewness (Rsk) is determined to be not more than zero, the strength of ends of the convex portions can be increased because the convex portions have a relatively flat end shape.

As a result, even if a strong external force is applied to the flat surface area 21 during mounting of the capillaries 15 on the flat surface area 21, chipping of the convex portions can be reduced. Thus, high reliability of the support 11 for capillaries can be maintained. Therefore, the skewness (Rsk) is preferable not more than zero. If chipping of the convex portions occurs, the width of concave portions of the flat surface area 21 is increased, and thus displacement of the center of the cross section of the capillaries 15 may be increased.

The skewness (Rsk) is more preferably not less than −2 because it makes the formation of the flat surface area 21 easier, thus the high productivity of the support 11 for capillaries can be achieved.

The skewness (Rsk) can be measured on the basis of, for example, ISO 4287: 1997 (Geometrical Product Specifications (GPS)-Surface texture: Profile method-Terms, definitions and surface texture parameters) or JIS B0601 (2001), herein incorporated by reference.

A part of the flat surface area 21 may be satisfied with the condition that the skewness (Rsk) is not more than 0. Preferably, not less than 50% area of the flat surface area 21 may be satisfied with the condition. More preferably, the entire of flat surfaces area 21 is satisfied with the condition.

Maximum Height of a Rolling Circle Waviness Profile ($W_{EM}$) of Support 11 for Capillaries The support 11 for capillaries preferably has a maximum height of a rolling circle waviness profile ($W_{EM}$) of not more than 1 μm. It becomes easier to allow the laser beam 19 to pass through the central positions of the cross section of a plurality of capillaries 15 by setting the $W_{EM}$ to be not more than 1 μm.

The maximum height of a rolling circle waviness profile ($W_{EM}$) is a parameter defined in ISO4287: 1997 (Geometrical Product Specifications (GPS)-Surface texture: Profile method-Definitions and designation of rolling circle waviness) or JIS B0610 (2001), herein incorporated by reference.

Figure 5A:
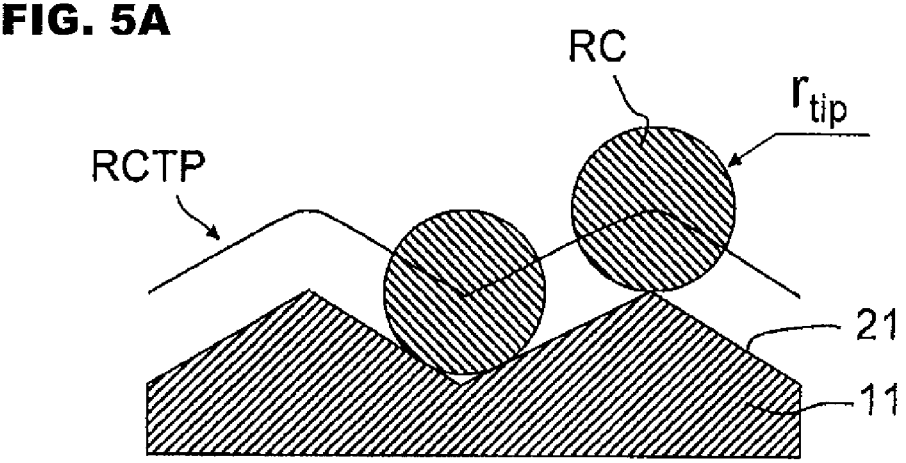
FIG. 5A shows a schematic view of the measurement method of maximum height of rolling circle waviness profile.

In order to determine the maximum height of a rolling circle waviness profile ($W_{EM}$), first, as shown in FIG. 5A, a rolling circle traced profile (RCTP) is measured. The rolling circle traced profile (RCTP) means a trajectory of the center of a rolling circle (RC) having a radius of $r_{tip}$ in the case where the rolling circle (RC) is moved along the flat surface area 21 of a support 11 for capillaries while being in contact with the flat surface area 21.

The RCTP shown in FIG. 5A is then converted to a digital form to determine a rolling circle waviness total profile (RCWTP) The length in the uniaxial direction of the RCWTP is a standard length lw.

Subsequently long-wavelength elements such as an arc are removed from the RCWTP using an optimized least-squares method, thereby determining a rolling circle waviness profile (RCWP).

Figure 5B:
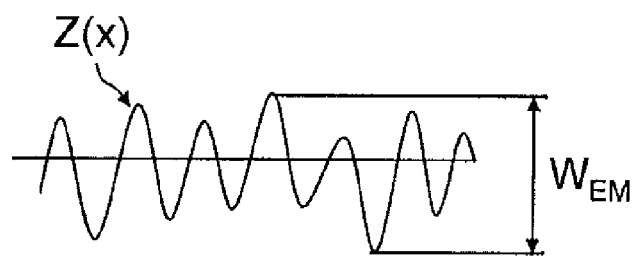
FIG. 5B shows a pattern diagram of a part of a filtered rolling circle waviness measured profile of the flat surface area of the support in accordance with an embodiment of the invention.

Next, elements longer than the waviness are removed from the RCWP using a λf filter, thus determining a filtered rolling circle waviness profile Z(x) shown in FIG. 5B. Herein, symbol λf represents a cutoff value of a filter that determines the boundary between a waviness element and an element having a wavelength longer than that of the waviness element as in the case of a λf profile filter described in ISO 4287 (1997). The cutoff value can be selected from 0.8 mm, 2.5 mm, 8 mm, and 25 mm.

As shown in FIG. 5B, the difference between the maximum and the minimum of the filtered rolling circle waviness profile Z(x) is defined as the maximum height of a rolling circle waviness profile ($W_{EM}$).

The reason why the $W_{EM}$ is determined to be not more than 1 μm is considered to be as follows. Each of the capillaries 15 has an outer diameter in the range of about 0.2 to 2 mm. Capillaries 15 each having an outer diameter in the range of about 0.2 to 0.4 mm are typically used. The $W_{EM}$ is generally measured by selecting a rolling circle having a radius of 0.08 mm, 0.25 mm, 0.8 mm, 2.5 mm, or the like and using it. A value that is the closest to the radius of the capillaries 15 is selected as the radius $r_{tip}$ of the rolling circle. It is believed that the value measured as the $W_{EM}$ is a value close to the difference between the highest position and the lowest position of the top portions of a plurality of capillaries 15 in a state in which the capillaries 15 are aligned on the support 11 for capillaries. When the $W_{EM}$ is determined to be not more than 1 μm, the positions of the top portions of the capillaries 15 do not vary significantly in the vertical direction. Accordingly, it becomes easier to allow the laser beam 19 to pass through the central positions of the cross section of the capillaries 15.

A part of the flat surface area 21 may be satisfied with the condition that $W_{EM}$ is not less than 1 μm. Preferably, not less than 50% area of the flat surface area 21 may be satisfied with the condition. More preferably, the entire of flat surfaces area 21 is satisfied with the condition.

Valley Level of Support 11 for Capillaries

In the support 11 for capillaries, the flat surface area 21 on which a capillary array including the capillaries 15 can be disposed in parallel, preferably has a valley level of not more than 45%. The valley level is represented by the following formula:

$$\text{Valley level} = \left[\left(\sum_{k=1}^{n} L_k\right) / L\right] \times 100\%$$

Here, L and $L_k$ in the above formula are defined as follows. First, a surface shape of the flat surface area 21 is linearly measured for a predetermined length along the surface, and the surface shape is drawn on the basis of the measurement, thus obtaining a concavo-convex shaped line. A hypothetical horizontal straight line crossing the concavo-convex shaped line is assumed. The position of the straight line is determined so that a total of first areas defined by the straight line and concave portions of the curve line and a total of second areas defined by the straight line and convex portions of the curve line are substantially equal. In this case, each length of the straight line corresponding to each of the first areas defined by the straight line and concave portions is represented by $L_k$, and the total length of the straight line is represented by L.

When the valley level defined above is set to be not more than 45%, the vertical positions of the capillaries 15 can be more satisfactorily aligned. This structure can contribute to an improvement in the performance of the capillary array structure 100. Note that the total length L of the straight line is preferably determined so that the concavo-convex shaped line includes at least five concave portions.

Figure 6A:
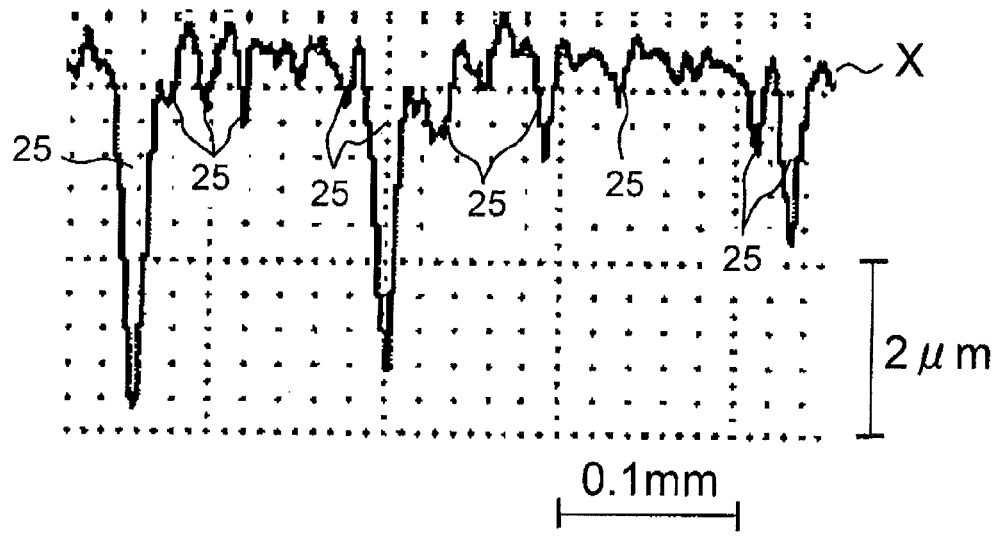
FIG. 6A shows a measured result of the surface shape in the flat surface area of the support in accordance with an embodiment of the invention.

A measurement example of the valley level will now be described. First, a concavo-convex shape of the flat surface area 21 of the support 11 for capillaries is measured with a non-contact surface roughness tester or the like. Thus, for example, a concavo-convex shaped line X shown in FIG. 6A is obtained. Subsequently, as shown in FIG. 6B, a horizontal straight line Z-Z' crossing the shaped line X is drawn so that the total of areas defined by the line Z-Z' and the convex portions of the shaped line X is equal to the total of areas defined by the line Z-Z' and the concave portions of the shaped line X.

Figure 6B:
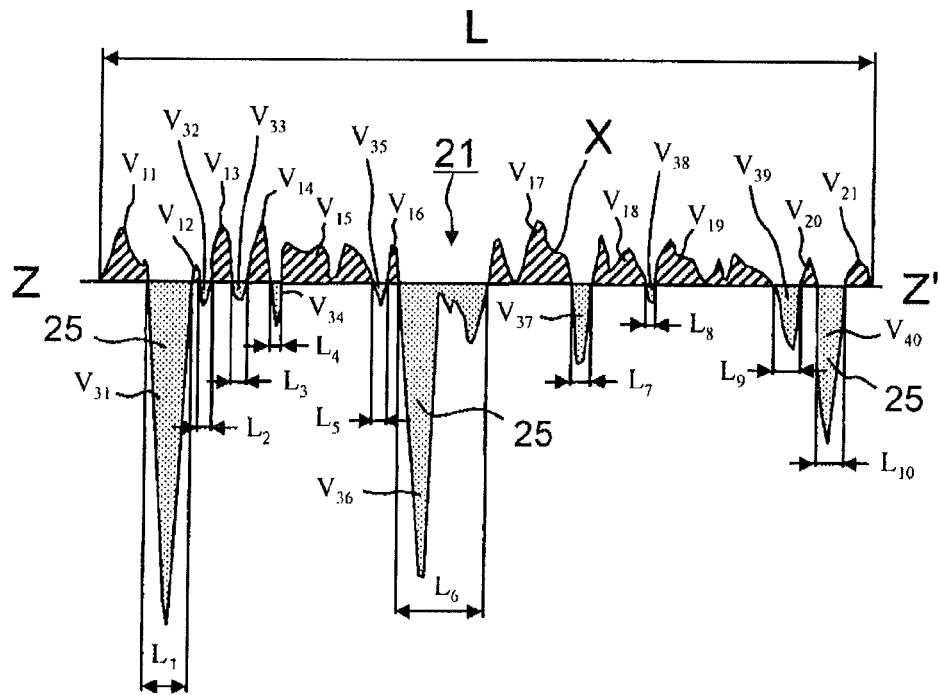
FIG. 6B illustrates the measurement method of valley level of the surface shape shown in FIG. 6A.

More specifically, in FIG. 6B, the position of the line Z-Z' is determined so as to satisfy the condition represented by formula (1):

$$(V_{11} + V_{12} + V_{13} + V_{14} + V_{15} + V_{16} + V_{17} + V_{18} + V_{19} + V_{20} + V_{21}) = \quad (1)$$
$$(V_{31} + V_{32} + V_{33} + V_{34} + V_{35} + V_{36} + V_{37} + V_{38} + V_{39} + V_{40})$$

In formula (1), each of $V_{11}$ to $V_{21}$ represents an area of a convex portion (hatched portion in FIG. 6B) with respect to the line Z-Z', and each of $V_{31}$ to $V_{40}$ represents an area of a concave portion (dotted portion in FIG. 6B) with respect to the line Z-Z' The length of the concave portions corresponds to each of the lengths represented by $L_1$ to $L_{10}$. The ratio of the sum of the lengths $L_1$ to $L_{10}$ to the length L is the valley level. The valley level (%) of the support 11 for capillaries is defined as formula (2):

$$\text{Valley level} = (L_1+L_2+L_3+L_4+L_5+L_6+L_7+L_8+L_9+L_{10})/L \times 100\% \quad (2)$$

Figure 7:
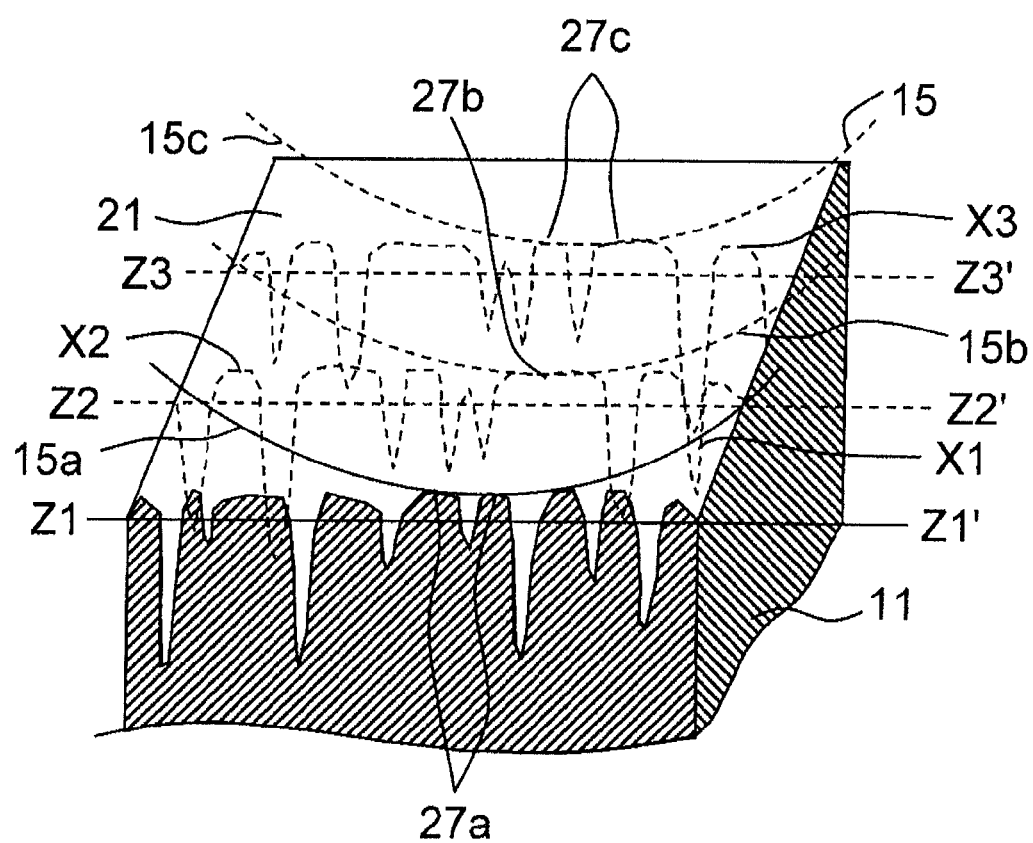
FIG. 7 illustrates a perspective and cross-sectional view of the configuration where the capillaries are disposed on the support in accordance with an embodiment of the invention.

A supplementary description will be made of the reason why waviness in the direction perpendicular to the flat surface area 21 of the capillaries 15 can be further decreased by controlling the valley level to be not more than 45%. FIG. 7 is a schematic enlarged view of the flat surface area 21 of the support 11 for capillaries, a part of which is shown by the cross section. Each of arcs 15a, 15b, and 15c shows a part of the circumference of a capillary 15 fixed on the flat surface area 21. Reference numerals X1, X2, and X3 denote the surface shapes of three positions of the flat surface area 21. The arc 15a is in contact with the surface shape X1, the arc 15b is in contact with the surface shape X2, and the arc 15c is in contact with the surface shape X3. The valley levels of the surface shapes X1, X2, and X3 are represented by a line Z1-Z1', a line Z2-Z2', and a line Z3-Z3', respectively. The valley levels of all the surface shapes X1, X2, and X3 are not more than 45%.

When the valley level is not more than 45%, as shown in FIG. 6B, the surface shape X includes many concave portions 25 having a small width and a large depth, and most of the surfaces of convex portions are generally flat. This also applies to the surface shapes X1, X2, and X3 shown in FIG. 7. Accordingly, even when the flat surface area 21 of the support 11 includes concave portions 25, the capillary 15 is not easily embedded in the concave portions 25. More specifically, for example, as shown in FIG. 7, even when the capillary 15 contacts with the surface shape X1 at two portion 27a and with the surface shape X3 at two portions 27c, since the capillary 15 contacts with the surface shape X2 at only one portion, a phenomenon in which the capillary 15 is embedded in the concave portions 25 can be reduced, and a shift in the position of the capillary 15 in the vertical direction can be further smaller.

More preferably, the valley level of the flat surface area 21 of the support 11 for capillaries is not more than 45%, and the surface roughness thereof is not more than 0.5 μm in terms of the arithmetic mean roughness (Ra) (based on ISO 4237-1997, herein incorporated by reference). In such a case, a shift in the position of the capillary 15 in the vertical direction can be further smaller. In particular, the valley level of the flat surface area 21 of the support 11 for capillaries is preferably not more than 40%, and the surface roughness thereof is preferably not more than 0.3 μm in terms of Ra. Accordingly, even if the outer diameter and the inner diameter of the capillary 15 are varied within, for example, about 5 μm, the laser beam 19 can be irradiated into the central portion of capillaries 15 with a high accuracy.

The lower limit of the valley level is preferably 10% to maintain high productivity.

The average of the width $L_k$ of the concave portions 25 present on the flat surface area 21 is preferably not more than 20 μm. In such a case, a phenomenon in which a capillary 15 is fitted in the concave portion 25 and bent can be reduced. Consequently, it is particularly easy to align a plurality of capillaries 15 so that the positions of the tops of the capillaries 15 are at a uniform distance from the flat surface area 21.

A part of the flat surface area 21 may be satisfied with the conditions that valley level is not more than 45% and/or not less than 10%. Preferably, not less than 50% area of the flat surface area 21 may be satisfied with the conditions. More preferably, the entire of flat surfaces area 21 is satisfied with the conditions.

Material of Support 11 for Capillaries

The support 11 for capillaries preferably comprises a ceramic sinter containing cordierite as a primary component; iron (Fe) in an amount of not less than 5% by mass in terms of $Fe_2O_3$; at least one element selected from nickel (Ni), cobalt (Co), manganese (Mn), and chromium (Cr) in a total amount of not more than 5% by mass (not including 0%) in terms of NiO, CoO, $MnO_2$, and $Cr_2O_3$, respectively, wherein the total content of iron, nickel, cobalt, manganese, and chromium is not more than 15% by mass of the support 11 in terms of $Fe_2O_3$, NiO, CoO, $MnO_2$, and $Cr_2O_3$, and the ceramic sintered body has a thermal expansion coefficient of not less than $0.1 \times 10^{-6}$/K and not more than $0.6 \times 10^{-6}$/K in the range of 20° C. to 60° C. In this case, the thermal expansion coefficient of the support 11 for capillaries is closer to that of the capillaries 15 made of quartz. Therefore, even when heat cycles due to an increase and a decrease in the temperature during irradiation of the laser beam 19 occur, a thermal stress applied to the capillaries 15 can be smaller to reduce the crack of the capillaries 15. In addition, the above composition can make it easier to provide the support 11 with a satisfactory black. Therefore, the use of this black ceramic sinter can effectively reduce transmission of the laser beam 19 through the support 11 for capillaries.

Since the ceramic material contains iron in an amount not less than 5% by mass of the support 11, a black ceramic sinter having a high Young modulus can be obtained. In addition to iron, since the ceramic material contains at least one element selected from nickel, cobalt, manganese, and chromium in a total amount of not more than 5% by mass (not including 0%) in terms of NiO, CoO, $MnO_2$, and $Cr_2O_3$, respectively, a support 11 for capillaries, the support being composed of a sinter in which chipping of crystalline particles of the ceramic does not easily occur during a polishing process, can be produced.

Furthermore, since the total content of iron, nickel, cobalt, manganese, and chromium in the sinter is not more than 15% by mass in terms of $Fe_2O_3$, NiO, CoO, $MnO_2$, and $Cr_2O_3$, it is easy to control the thermal expansion coefficient of the support 11 for capillaries to be not less than $0.1 \times 10^{-6}$/K and not more than $0.6 \times 10^{-6}$/K. Accordingly, the thermal expansion coefficient of the support 11 for capillaries can be controlled to be a value substantially the same as that of quartz glass. Since the thermal expansion coefficient of the support 11 for capillaries is close to that of the capillaries 15 made of quartz, even when heat cycles due to an increase and a decrease in the temperature during irradiation of the laser beam 19 occur, a thermal stress applied to the capillaries 15 can be smaller to reduce the crack of the capillaries 15.

The thermal expansion coefficient varies in accordance with the sintering condition or the like. Therefore, the total content of iron, nickel, cobalt, manganese, and chromium in the support 11 is preferably not less than 10.7% by mass and not more than 14.0% by mass, more preferably more than 10.8% by weight and not more than 13.7% by mass in terms of $Fe_2O_3$, NiO, CoO, $MnO_2$, and $Cr_2O_3$, respectively.

The thermal expansion coefficient can be measured using, for example, a laser thermal expansion meter (Model LIX-1 manufactured by ULVAC-RIKO, Inc.). A sample cut out from a support 11 for capillaries can be used as a sample for measuring the thermal expansion coefficient. The sample has dimensions of, for example, a length in the range of 10 to 15 mm, a width in the range of 3 to 4 mm, and a thickness in the range of 2 to 3 mm, and the thermal expansion coefficient in the longitudinal direction of the sample is measured. Each end in the longitudinal direction of the sample may be processed to have a quadrangular pyramid so that the sample is set in a point contact manner when being fixed in a measurement device. In this case, errors of analysis caused by a difference in the method of fixing a sample can be reduced.

The temperature range of the thermal expansion coefficient of the support 11 for capillaries is specified in the range of 20° C. to 60° C. This is because the temperature of the support 11 for capillaries used in a DNA analyzer including the capillary array structure 100 particularly tends to be changed in this range.

When the thermal expansion coefficient of the support 11 for capillaries is controlled to be not less than $0.1 \times 10^{-6}$/K and not more than $0.6 \times 10^{-6}$/K in this temperature range, the thermal expansion coefficient of the support 11 for capillaries has the thermal expansion coefficient close to that of quartz glass. Accordingly, this material is the most suitable for an alternative material for black quartz glass. More preferably, the thermal expansion coefficient of the support 11 for capillaries is in the range of not less than $0.1 \times 10^{-6}$/K and not more than $0.5 \times^{-6}$/K.

Regarding the thermal expansion coefficient of the support 11 for capillaries specified in the embodiment, the upper limit of the thermal expansion coefficient is closer to a typical thermal expansion coefficient of quartz glass (about $0.5 \times 10^{-6}$/K), rather than the lower limit thereof. The reason for this is that, in a DNA analyzer or the like, an analysis of samples is often performed in the range of room temperature (about 25° C.) to a temperature somewhat higher than room temperature, and thus, reliability of joining in the range of 20° C. to 60° C. is required.

Furthermore, in the case where the support 11 for capillaries contains cordierite as a primary component, when the ceramic material of the support 11 is sintered once, the shape and color of the ceramic material are hardly changed as long as the temperature is not again increased to about 1,400° C., which is the melting temperature of cordierite. That is, when a support 11 is used at high temperatures of 1,000° C. or higher, problems, such as softening and whitening due to crystallization, which inevitably occur at present as long as quartz glass is used, can be solved by using a black support 11 for capillaries.

Cordierite, which is contained as a primary component, is known as a material having a particularly low thermal expansion coefficient among ceramic sintered body. By dispersing a compound having a high thermal expansion coefficient and containing iron and at least one element selected from nickel, cobalt, manganese, and chromium in grain boundaries of cordierite, not only the thermal expansion coefficient can be adjusted to a desired value, but also the cordierite can be blackened. By blackening cordierite, irregular reflection of incident light can be decreased to decrease the reflection coefficient.

Figure 8:
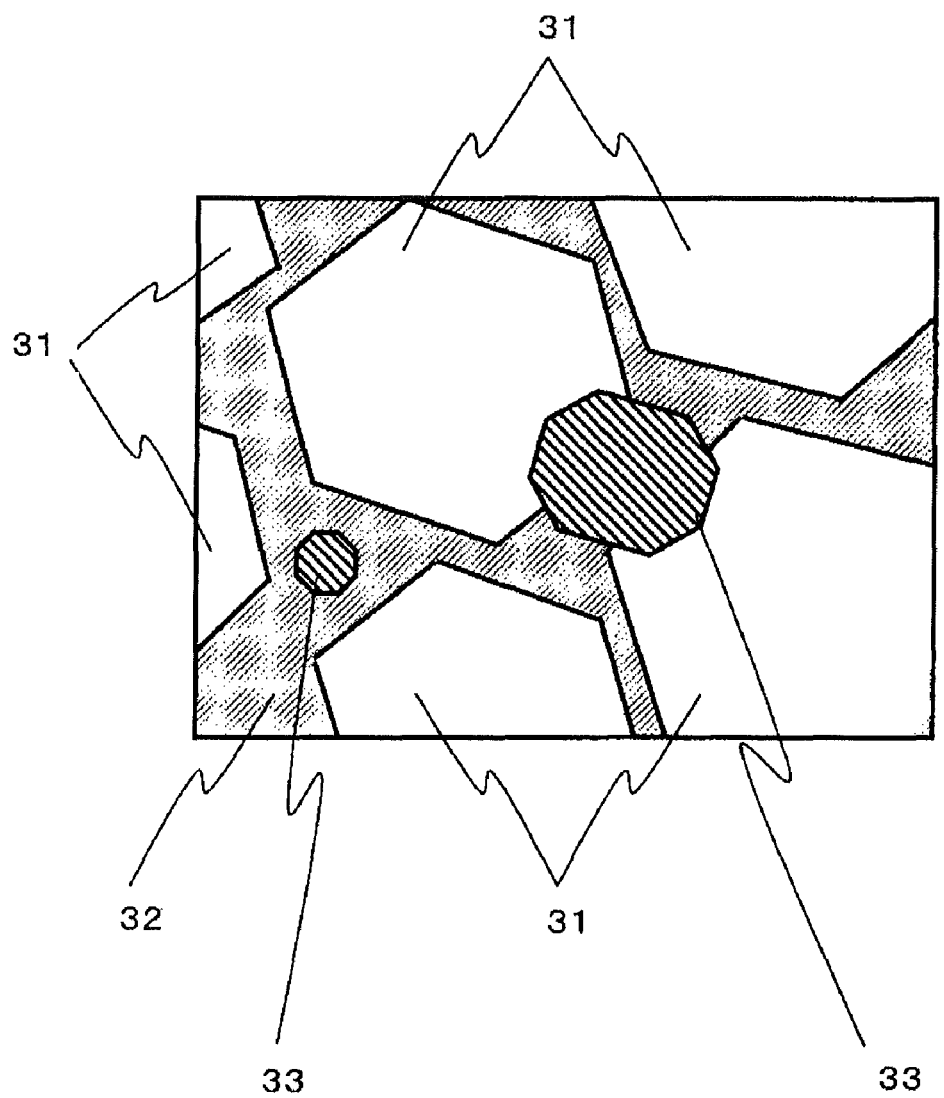
FIG. 8 illustrates a magnified view of a structure of the ceramic sinter constituting the support in accordance with an embodiment of the invention.

FIG. 8 is a schematic view showing an example of the structure of a ceramic sinter in the case where the support 11 for capillaries in the embodiment comprises a black ceramic sintered body containing cordierite as a primary component. This sinter includes crystal grains 31 made of cordierite, and glass 32 that comprises elements of manganese (Mg), silicon (Si), aluminum (Al) oxygen (O) and the like and that is disposed in the grain boundaries of the crystal grains 31. Furthermore, an oxide complex 33 mainly containing iron is segregated in the crystal grain boundaries. This segregation means that the oxide compound 33 is present in the glass 32 disposed between the crystal grains 31 of cordierite, or the oxide compound 33 is present in the grain boundaries of the crystal grains 31 of cordierite and is adjacent to the crystal grains 31 of cordierite. The oxide compound 33 is composed of oxides such as $MgFeAlO_4$, $MgFe_2O_4$, $Mg(AlFe)_2O_4$, and $FeAl_2O_4$. A support 11 for capillaries having a desired thermal expansion coefficient curve can be produced by changing the content of the oxide compound 33.

The iron content in the support 11 is preferably not less than 7% and not more than 12% by mass in terms of $Fe_2O_3$. At an iron content within this range, iron easily forms an oxide compound 33 such as $MgFeAlO_4$, $MgFe_2O_4$, $Mg(AlFe)_2O_4$, and $FeAl_2O_4$. Also, an iron content of not more than 12% by mass is preferable because the thermal expansion coefficient may be in an appropriate range to reduce generating microcracks at the interface of the oxide compound 33. An iron content of not less than 7% by weight is also preferable because the mechanical strength of the ceramic material, in particular, the Young's modulus may be enhanced.

In addition, in the case where the ceramic sintered body contains at least one element selected from nickel, cobalt, manganese, and chromium, the glass 32 also contains at least one element selected from nickel, cobalt, manganese, and chromium. Accordingly, detachment of crystal particles can be reduced in a grinding process of the ceramic sintered body, and thus a processed surface having a small surface roughness can be obtained. The reason for this is considered to be as follows. The adhesion strength between the crystal grains 31 of cordierite and the glass 32 is improved because at least one element selected from nickel, cobalt, manganese, and chromium is contained in the glass 32.

As materials of the support 11, the black ceramics disclosed in Japanese Unexamined Patent Application Publication No. 2001-19540, Japanese Unexamined Patent Application Publication No. 2001-302341, and Japanese Unexamined Patent Application Publication No. 2002-167267 may be used.

Japanese Unexamined Patent Application Publication No. 2001-19540 discloses a black ceramic sintered body having an absolute value of the thermal expansion coefficient at room temperature of not more than $0.6 \times 10^{-6}$/K, an elasticity modulus (Young's modulus) of not less than 100 GPa, and a specific stiffness (Young's modulus/specific gravity) of not less than 40 GPa·$cm^3$/g. This black ceramic sintered body has a chemical composition containing 8.0% to 17.2% by weight of MgO, 22.0% to 38.0% by weight of $Al_2O_3$, 49.5% to 65.0% by weight of $SiO_2$, total 0.1% to 2% by weight of at least one transition element in terms of an oxide thereof, and 0% to 2.5% by weight of $Li_2O$ and satisfying the relationships of $(SiO_2-8 \times Li_2O)/MgO \geq 3.0$ and $(SiO_2-8 \times Li_2O)/Al_2O_3 \geq 1.2$ by weight.

Japanese Unexamined Patent Application Publication No. 2001-302341 discloses a dense sintered body of black cordierite containing cordierite as primary crystals, at least one type of crystal other than cordierite, and a colorable pigment that develops black and that is incorporated in the crystal other than cordierite in an amount in the range of 1% to 10% by weight. The dense sintered body of a black cordierite has a thermal expansion coefficient at room temperature in the range of $-0.1 \times 10^{-6}$/K to $+0.1 \times 10^{-6}$/K and a value calculated by dividing the Young's modulus by the bulk density (Young's modulus/bulk density) of not less than $5 \times 10^7$ $m^2/s^2$. Examples of the composition of the colorable pigment include a colorable pigment composed of only an iron oxide, and a colorable pigment composed of an oxide containing iron, chromium, and cobalt.

Japanese Unexamined Patent Application Publication No. 2002-167267 discloses a black ceramic with a low thermal expansion coefficient containing cordierite as a primary component and at least one metal selected from the group of transition metals consisting of copper, cobalt, chromium, nickel, iron, manganese, titanium, vanadium, niobium, molybdenum, and tungsten as a coloring agent in an amount in the range of 0.1% to 10% by weight in terms of an oxide. The black ceramic has a thermal expansion coefficient of not more than $1 \times 10^{-6}$/K in the range of 10° C. to 40° C., a relative density of not less than 95%, and a Young's modulus of not less than 100 GPa.

Brightness of Support 11 for Capillaries

The ceramic member constituting the support 11 for capillaries preferably has a brightness L* noted by an L*a*b* method (corresponding international standard: ICS 17. 180. 20) of not more than 30, and a total reflection coefficient of not more than 7% in the wavelength range of 350 to 750 nm. The support 11 for capillaries having such characteristics can function as a member in which the irregular reflection and transmission of a laser beam can be particularly reduced.

Chromaticness of Support 11 for Capillaries

Furthermore, the absolute value of a chromaticness b* noted by an L*a*b* method of the ceramic member constituting the support 11 for capillaries is preferably not more than 5. When the chromaticness b* is not more than 5, a bluish tone of the ceramic member becomes a more blackish tone. Accordingly, the total reflection coefficient can be further decreased. In addition, when particles such as contaminations are adhered on the ceramic member, the particles can be easily distinguished.

In addition, the support 11 for capillaries preferably has a porosity of not more than 0.1% by volume. The reason for this is as follows. The flat surface area 21 of the support 11 for capillaries is formed by a polishing process. When the porosity is not more than 0.1% by volume, the number of open pores extending from the inside of the sintered body to the flat surface area 21 is reduced by the polishing process. As a result, bending of a capillary 15 along such open pores can be suppressed. In order to produce a support 11 for capillaries having a porosity of not more than 0.1% by volume, in addition to a normal sintering in an oxidizing atmosphere, a process of hot isostatic pressing (HIP) may then be performed.

Method of Producing Case 10 for Capillaries and Support 11 for Capillaries

A method of producing a case 10 for capillaries will now be described specifically.

As starting materials, powders; a solvent such as water; and a dispersant such as a surfactant are weighed. As materials of powder, a cordierite powder, an iron oxide powder, a nickel oxide powder, and the like may be used. These starting materials are mixed with a ball mill, a vibrating mill, a bead mill, or the like, and the mixture is then pulverized. Examples of a pulverizing medium include balls and beads made of alumina or zirconia. An organic binder is mixed with the resulting slurry, and the mixture is sprayed with a spray dryer, dried, and granulated to prepare a granulated powder. The resulting granulated powder is filled in a die and molded with a press machine under pressure, thus prepare a compact having a predetermined shape. The shape of the compact is a shape for producing a support 11 for capillaries, a side wall 13, or a lid 17. The compact is then sintered in an oxygen-containing gas at a temperature in the range of 1,300° C. to 1,400° C. to prepare a cordierite sinter. The resulting sinter is processed to have the shape of the support 11 for capillaries, the side wall 13, or the lid 17. The support 11 for capillaries is joined with the side walls 13 with glass to prepare a case for capillaries shown in FIG. 1A. The lid 17 is preferably attached to the side walls 13 after capillaries 15 are fixed on a flat surface area 21.

In this method, the flat surface area 21 of the support 11 for capillaries is processed by lapping as follows.

A first method is as follows. A plurality of ceramic sintered bodies to be processed is held with a work, and the work is placed on a disc-shaped surface plate. The ceramic sinters are pressed onto the surface plate, and a polishing agent prepared by dispersing a loose abrasive in an aqueous polishing liquid (e.g., water containing a surfactant and a rust-preventing agent) is dripped on the surface plate. The surface plate is rotated in this state, and the work is further rotated and revolved on the surface plate. Thus, the surface plate and the ceramic sintered bodies are slid via the loose abrasive. Accordingly, the surfaces of the ceramic sintered bodies are removed with the loose abrasive to smoothen the surfaces. The loose abrasive used in this method is preferably diamond abrasive grains or green carborundum (GC) abrasive grains having a small grain size.

A second method is as follows. A plurality of ceramic sintered bodies fixed with a work is placed on a surface plate made of a material in which fine diamond abrasive grains are bonded with a metal such as a Cu—Sn alloy. The work is pressed onto the surface plate, and the surface plate is rotated and the work is further rotated and revolved while an aqueous polishing liquid is supplied on the surface plate. Thus, surfaces of the ceramic sintered bodies are removed, thus smoothing the surfaces.

This lapping process is performed until the flatness of the flat surface area 21 becomes not more than 0.02 mm, and the mean spacing of waviness motifs (AW) in the flat surface area 21 becomes not more than 100 μm.

In order to control the skewness (Rsk) of the flat surface area 21 to be not more then zero, for example, after the above lapping process, an additional lapping process is performed using diamond abrasive grains having a maximum grain size of not more than 1 μm and a lubricant such as olive oil. In this case, the lubricant and the loose abrasive are interposed between the surface plate and the ceramic sintered bodies. The lubricant is used in order to maintain a high holding force for holding the diamond abrasive grains having a small grain size between the surface plate and the ceramic sintered bodies.

Furthermore, in order to control the maximum height of a rolling circle waviness profile ($W_{EM}$) of the flat surface area 21 to be not more than 1 μm, for example, a lapping process is further performed using diamond abrasive grains having a maximum grain size of not more than 0.5 μm and a lubricant. In this case, the lubricant and the loose abrasive are interposed between the surface plate and the ceramic sinters. The reason for the use of the lubricant is the same as that described above.

In order to control the valley level of the flat surface area 21 to be not more than 45%, for example, buffing is further performed, that is, polishing is further performed with a soft material such as a cloth to which polishing abrasive grains are attached.

In the method of producing the support for capillaries of the embodiment, the temperature during sintering is maintained in the range of 1,300° C. to 1,400° C., and the temperature is then decreased at a cooling rate of 135° C./h or lower. In such a case, the ratio (A/B) of a peak intensity A of a peak (lattice spacing d=around 2.51 Å) obtained by X-ray diffractometry with a Cu—Kα radiation of the oxide compound 33 containing iron to a peak intensity B of a peak (lattice spacing d=around 8.45 Å) obtained by X-ray diffractometry of cordierite can be controlled to be not more than 0.5. Consequently, the thermal expansion coefficient of the support for capillaries can be controlled to be not less than $0.1 \times 10^{-6}$/K and not more than $0.6 \times 10^{-6}$/K. A sintering temperature of lower than 1,300° C. is not preferable because the porosity of the support for capillaries is increased. A sintering temperature of higher than 1,400° C. is also not preferable because the support for capillaries may be softened and melted. The sintering temperature is more preferably in the range of 1,320° C. to 1,380° C.

The thermal expansion coefficient of the oxide compound 33 containing iron is larger than that of cordierite. Therefore, by controlling the above peak ratio to be not more than 0.5, the thermal expansion coefficient can be stabilized and a high strength and a high Young's modulus of the support for capillaries can be maintained. The support for capillaries produced by the method of producing a support for capillaries of the embodiment has a three-point bending strength higher than 69 MPa, which is the three-point bending strength of quartz, and a Young's modulus higher than 74 GPa, which is the Young's modulus of quartz. Accordingly, the support for capillaries produced by the method of the embodiment has satisfactory characteristics required for an alternative material for quartz glass.

The support for capillaries thus produced, which is made of a black ceramic sintered body, is suitably used as a support for capillaries in which capillaries for an electrophoresis apparatus installed in a DNA analyzer are aligned and the capillaries are irradiated with a laser beam. In addition, the color tone of the support for capillaries produced as described above hardly changes with time, and thus, the support can be used for a long period of time.

Figure 9:
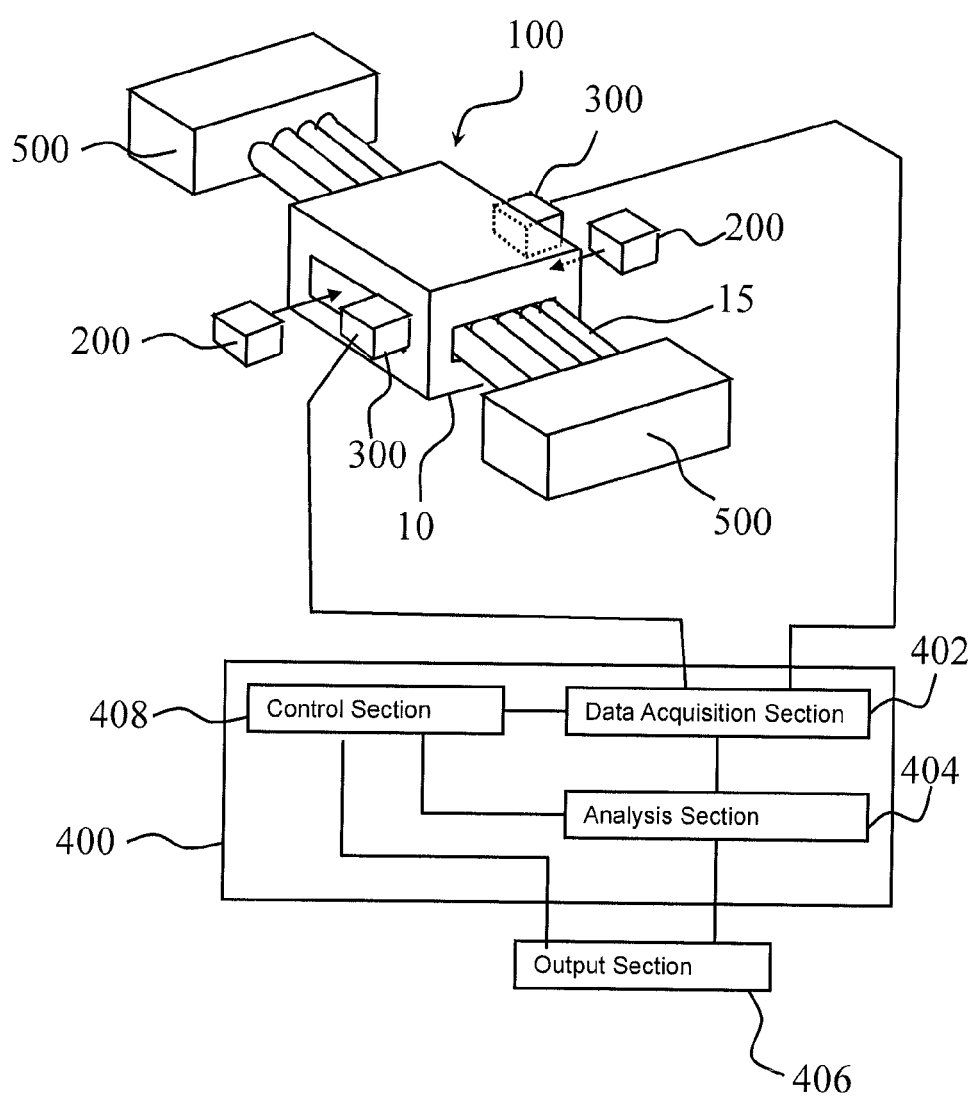
FIG. 9 illustrates a schematic view of an analysis apparatus including the case in FIG. 1A.

FIG. 9 is a schematic view of an analysis apparatus using the case 10. An analysis apparatus 1 includes the capillary array structure 100, a laser beam emitting device 200, a detector 300, an analyzer 400 and a fluidization unit 500. As described above, the capillary array structure 100 comprises the case 10 including the capillaries 15 and the side walls. The fluidization unit 500 supplies electrophoretic mediums containing measurement samples into the capillaries 15 and applies voltage to the electrophoretic mediums to electrophorese them. The laser beam emitting device 200 irradiates the capillaries 15 having the electrophoresed measurement samples with the laser beam 19 from the direction orthogonal to the longitudinal direction of the capillaries 15. As the laser beam emitting device 200, any types of laser beam emitting device 200 may be used. In the embodiment, an argon laser is used as a laser beam emitting device. When laser beam 19 is transmitted through the capillaries 15 and the measurement samples are irradiated with the laser beam 19, the measurement samples emit the fluorescence. The detector 300 receives both the fluorescence from the measurement samples and the transmitted light through the capillaries 15 and outputs a detection signal is corresponding to intensity of the received light. The analyzer 400 includes a data acquisition section 402, an analysis section 404 and an output section 406. The data acquisition section 402 acquires the detection signal output from the detector 300. The analysis section 404 processes the detection signal acquired by the data acquisition section 402 and outputs desired analysis results of the samples. The output section 406 such as a monitor or the like, displays and outputs the results analyzed by the analysis section 404. The analyzer 400 further includes a control section 408 such as a CPU or the like, connected to the data acquisition section 402, analysis section 404 and output section 406 so as to control operations of each section with the control section 408. Furthermore, the control section 408 is connected to the laser beam emitting device 200, detector 300, analyzer 400 and sample fluidization unit (the connecting lines are not illustrated), respectively. The control section 408 controls operations of the analysis apparatus 1.

The analysis apparatus 1 can analyze the measurement samples as follows. First, the fluidization unit 500 supplies the electrophoretic mediums containing the measurement samples into the capillaries 15 and electrophoreses the electrophoretic medium by applying voltage to the electrophoretic medium. In that state, the laser beam emitting device 200 irradiates the capillaries 15 with the laser beam 19. The detector 300 receives both the transmitted light of the laser beam 19 through the capillaries 15 and the fluorescence emitted from the measurement sample irradiated with the laser beam 19 and outputs the detection signal corresponding to intensity of the received light. The data acquisition section 402 of the analyzer 400 acquires the detection signal output from the detector 300 and outputs to the analysis section 404. The analysis section 404 processes the detection signal acquired by the data acquisition section 402 and outputs the desired analysis results of the samples. The output section 406 displays and outputs the results analyzed by the analysis section 404. The case 10 includes the ceramic member having the flat surface area on which the capillaries can be arranged. The flat surface area has a flatness of not more than 0.02 mm and a mean spacing of waviness motifs (AW) at the flat surface of not more than 100 μm so that a displacement of each capillary can be kept small with respect to the perpendicular direction. Also, scattering of the laser beam can be lessened because in the embodiment, the case 10 is black.

The invention is not limited to the above embodiments including the above Japanese Unexamined Patent Application Publications.

EXAMPLES

Samples of a case 10 for capillaries were produced by the following method.

First, 85% to 94.9% by mass of a cordierite powder and 4.9% to 15% by mass of at least one powder serving as a blackening agent selected from an iron oxide powder, a nickel oxide powder, a chromium oxide powder, a cobalt oxide powder, and a manganese oxide powder were prepared and blended. The mixed powder was then mixed with water by a wet process using a ball mill, and the resulting mixture was then pulverized to prepare a slurry.

As organic binders, water-soluble polyvinyl alcohol and an acrylic polymer compound were then added to the resulting slurry. The mixture was dried and granulated by a spray drying method with a spray drier, thus preparing a granulated powder for molding. A plurality of Compacts 1, a plurality of Compacts 2, and a plurality of Compacts 3, which had dimensions described below were molded by a pressure molding using the prepared granulated powder.

Compact 1 for a Support 11 Used for Supporting Capillaries 15:

30 mm (in the width direction of a capillary array)×30 mm (in the longitudinal direction of a capillary)×4 mm (in thickness)

Compact 2 for a Side Wall 13 (Four Compacts Constitute One Unit):

5 mm (in the width direction of a capillary array)×8 mm (in the longitudinal direction of a capillary)×8 mm (in height)

Compact 3 for a Lid 17:

35 mm (in the width direction of a capillary array)×30 mm (in the longitudinal direction of a capillary)×4 mm (in thickness)

Compacts 1, 2, and 3 were then maintained in air in the range of 1,300° C. to 1,400° C., and the temperature was then decreased at a cooling rate of 100° C./h to prepare cordierite sintered bodies 1, 2, and 3. The surfaces of the sintered bodies 1, 2, and 3 were processed to prepare supports 11 for capillaries, side walls 13, and lids 17. A flat surface area 21 of each of the supports 11 for capillaries was lapped while abrasive grains including diamond abrasive grains having a grain size shown in Table 2 and an aqueous polishing liquid were supplied between the flat surface area 21 of a sinter 1 and a surface plate made of cast iron and having a small flatness. Furthermore, for some samples (sample Nos. 2 to 10 and Sample Nos. 17 and 18 in Tables 1 and 2), a lapping process was performed using diamond abrasive grains having a maximum grain size of 1 µm and an aqueous polishing liquid, a lapping process in which a sintered body 1 was slid with cast iron was then further performed in a state in which diamond abrasive grains having the grain size shown in Table 2 and a lubricant used as a polishing liquid are interposed between the sintered body 1 and the cast iron. For some samples (sample Nos. 5 to 11 and Sample Nos. 17 and 18 in Tables 1 and 2), a lapping process was performed using diamond abrasive grains having a maximum grain size of 1 µm and an aqueous polishing liquid, a lapping process was then further performed using diamond abrasive grains having a maximum grain size of not more than 1 µm and a lubricant, and buffing was further performed with a cloth to which diamond abrasive grains were attached.

The aqueous polishing liquid used in the example was water containing a mineral oil, a surfactant, a rust-preventing agent, an antiseptic, and the like in a total content in the range of 2% to 5% by mass.

The following measurements were performed using a plurality of samples each including the prepared support 11 for capillaries.

The contents of iron, nickel, chromium, manganese, and cobalt in the supports 11 for capillaries were measured. The contents were measured with an ICP emission spectrometer, and the results were calculated in terms of $Fe_2O_3$, NiO, $Cr_2O_3$, $MnO_2$, and CoO, respectively.

The flatness, the mean spacing of waviness motifs (AW), and the arithmetic mean roughness (Ra) of the flat surface area 21 of each of the supports 11 for capillaries were measured. These values were measured with a surface roughness tester SV-600 manufactured by Mitsutoyo Corporation. The skewness (Rsk) and the maximum height of a rolling circle waviness profile ($W_{EM}$) of the flat surface area 21 were measured with a surface roughness tester SV-C3100S4 manufactured by Mitsutoyo Corporation. Regarding the radius $r_{tip}$ of the rolling circle, 0.08 mm was selected.

The valley level of the flat surface area 21 of each of the supports 11 for capillaries was measured as follows. Specifically, a roughness curve (shaped line) of the surface of the flat surface area 21 was enlarged at a magnification ratio of 5,000 in the vertical direction, and at a magnification ratio of 200 in the direction parallel to the flat surface area 21. The measurement distance was determined as a straight line having a length of 1 mm along the flat surface area 21. The valley level of the prepared roughness curve (shaped line) was measured by the method described above.

In addition, an argon laser beam having a wavelength of 488 nm was irradiated on the flat surface area 21 of each of the supports 11 for capillaries in the vertical direction, thus determining whether or not the laser beam was transmitted through each of the supports 11 for capillaries.

The thermal expansion coefficient of each of the supports 11 for capillaries was measured in the temperature range of 20° C. to 80° C. The thermal expansion coefficient was measured with a laser thermal expansion meter (Model LIX-1 manufactured by ULVAC-RIKO, Inc.) using a sample for a thermal expansion coefficient measurement with dimensions of 4 mm×3 mm×15 mm prepared by processing each of the supports 11 for capillaries.

The brightness L* and the chromaticness b* of each of the supports 11 for capillaries were measured with a color-difference meter (spectroscopic color-difference meter NF-777 manufactured by Nippon Denshoku Industries Co., Ltd.).

In addition, the total reflection coefficient of each of the supports 11 for capillaries was measured. The measurement was performed on the basis of ISO/DIS7724-1: 1997, ISO/DIS7724-2: 1997 or JIS Z 8722: 2000 using a spectrocolorimeter CM-3700D manufactured by Konica Minolta Holdings, Inc. in the range of 350 to 750 nm, and the maximum value was defined as the total reflection coefficient.

The ratio (A/B) of the height of a peak A (lattice spacing d=around 2.5 Å) of $MgFeAlO_4$ of each of the supports 11 for capillaries to the height of a peak B (lattice spacing d=around 8.45 Å) of cordierite was measured. The measurement was performed with an X-ray diffractometer RINTI400V manufactured by Rigaku Corporation. More specifically, the ratio (A/B) was determined by X-ray diffractometry with a Cu—Kα radiation.

In addition, a cross section of each of the supports 11 for capillaries was polished to form a mirror-finished surface. The surface was observed with a scanning electron microscope (SEM) at a magnification ratio of 5,000 to examine the presence or absence of microcracks in the sintered body.

Furthermore, each of the supports 11 for capillaries was formed into a quadrangular prism having dimensions of 3 mm×4 mm×10 mm. The prepared sample was joined with a quartz glass sample having the same dimensions to evaluate the joining property. More specifically, a binder composed of a low-melting glass was applied on a surface of the quadrangular prism sample prepared by processing the support 11 for capillaries, and the quartz glass sample was placed on the binder. The resulting sample was heated at 800° C. for 10 minutes to melt the low-melting glass, thus joining the sample obtained from the support 11 and the quartz glass sample with the low-melting glass. The joined interface of the joined product was observed with a metallurgical microscope at a magnification ratio of 500 to examine whether or not a space was formed at the joined interface.

A support 11 for capillaries was joined to side walls 13 using a low-melting glass to prepare a joined product. Subsequently, 48 quartz glass capillaries 15 each having an outer diameter of 0.3 mm and an inner diameter of 0.1 mm (wherein a polyimide coated on the surfaces of the capillaries-had been removed) were disposed on a flat surface area 21 of the joined product so as to be adjacent to each other. In this state, a powder of Teflon (registered trademark) AF1600 manufactured by DuPont was tentatively filled on the capillaries 15 aligned on the flat surface area 21, and the joined product was heated to 300° C. Subsequently, a pressure was applied in a state in which the capillaries 15 were in contact with the flat surface area 21. Thus, spaces between the capillaries 15 and the entire part over the upper portion of the capillaries 15 were filled with the Teflon (registered trademark) resin. In this state, the positions of the tops (disposed adjacent to a lid 17) of the capillaries 15 disposed near the light path of a laser beam 19 were measured with a dial gauge to determine the maximum of the difference in the positions of the tops of the capillaries 15 in the direction perpendicular to the flat surface area 21 (i.e., the maximum of the difference in vertical positions among capillaries 15).

Figure 1B:
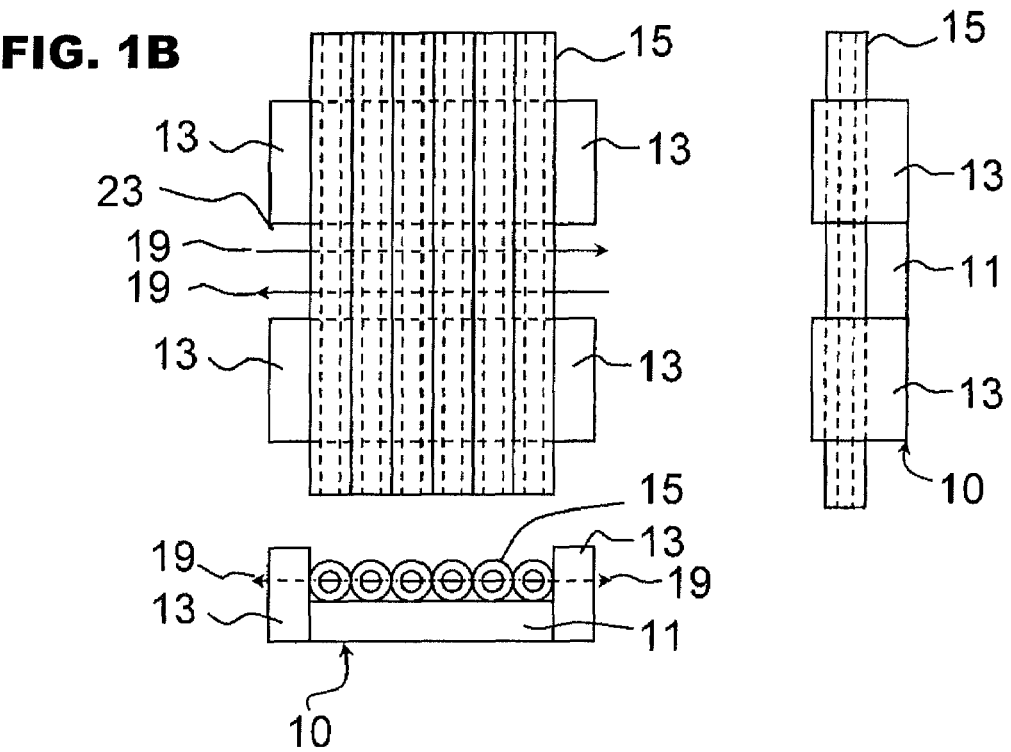
FIG. 1B illustrates both a plan view and a side view of the capillary array structure in FIG. 1A where a lid is removed.

The side walls 13 were then bonded to the lid 17 using an adhesive, thus preparing a capillary array structure shown in FIG. 1B. In a state in which the plurality of capillaries 15 were filled with a liquid having the same refractive index as that of quartz, an argon laser beam having a wavelength of 488 nm was irradiated from an opening 23 of the above capillary array structure and passed through the insides of the capillaries 15 filled with the liquid, thus examining whether or not the laser beam was accurately detected from another opening 23.

Tables 1 and 2 show the results except for the values of A/B and the presence or absence of microcracks in the samples. In Sample Nos. 1 to 18, the value of A/B was not more than 0.5. In addition, no cracks were observed in Sample Nos. 1 to 18.

TABLE 1

| Sample No. | Color tone | Flatness mm | AW μm | Rsk | $W_{EM}$ μm | Valley level % | Ra μm | Composition of blackening agent (% by mass) | | | | | |
|---|---|---|---|---|---|---|---|---|---|---|---|---|---|
| | | | | | | | | $Fe_2O_3$ | NiO | CoO | $MnO_2$ | $Cr_2O_3$ | Total |
| 1 | Black | 0.02 | 50 | 0.1 | 0.56 | 50 | 0.32 | 5 | 2 | 0 | 0 | 0 | 7 |
| 2 | Black | 0.02 | 45 | −0.1 | 1.2 | 50 | 0.34 | 7.5 | 0 | 0 | 0 | 0.5 | 8 |
| 3 | Black | 0.02 | 38 | −0.3 | 1.04 | 46 | 0.42 | 6 | 0 | 3 | 0 | 0 | 9 |
| 4 | Black | 0.02 | 35 | −0.9 | 1.04 | 46 | 0.43 | 7 | 0 | 0 | 3 | 0 | 10 |
| 5 | Black | 0.002 | 34 | −1.3 | 0.98 | 29 | 0.23 | 7.5 | 3 | 0 | 0 | 0 | 10.5 |
| 6 | Black | 0.01 | 27 | −2 | 0.39 | 15 | 0.21 | 7.5 | 3 | 0 | 0.5 | 0 | 11 |
| 7 | Black | 0.02 | 31 | −1 | 0.37 | 36 | 0.2 | 7 | 4 | 0 | 0.9 | 0 | 11.9 |
| 8 | Black | 0.01 | 22 | −0.8 | 0.33 | 35 | 0.23 | 10 | 3 | 1 | 0 | 0.5 | 14.5 |
| 9 | Black | 0.01 | 30 | −0.7 | 0.21 | 39 | 0.18 | 10.5 | 3 | 1 | 0.5 | 0 | 15 |
| 10 | Black | 0.01 | 43 | −0.5 | 0.1 | 39 | 0.17 | 14 | 1 | 0 | 0 | 0 | 15 |
| 11 | Black | 0.02 | 46 | 0.1 | 0.43 | 42 | 0.24 | 4.3 | 4 | 0 | 0.2 | 0 | 8.5 |
| 12 | Black | 0.02 | 43 | 0.2 | 0.66 | 51 | 0.38 | 7 | 5.5 | 0 | 0 | 0.1 | 12.6 |
| 13 | Black | 0.02 | 42 | 0.1 | 0.68 | 48 | 0.39 | 14 | 1 | 0.2 | 0.2 | 0 | 15.4 |
| 14 | Black | 0.02 | 55 | 0.2 | 0.7 | 46 | 0.4 | 7 | 4 | 0 | 0.9 | 0 | 11.9 |
| 15 | Black | 0.02 | 73 | 0.2 | 0.84 | 46 | 0.43 | 7 | 4 | 0 | 0.9 | 0 | 11.9 |
| 16 | Black | 0.02 | 100 | 0.3 | 1.1 | 53 | 0.5 | 7 | 4 | 0 | 0.9 | 0 | 11.9 |
| 17 | Black | 0 | 4 | −0.1 | 0.03 | 38 | 0.02 | 7 | 4 | 0 | 0.9 | 0 | 11.9 |
| 18 | Black | 0.02 | 89 | 0 | 1 | 38 | 0.64 | 7 | 4 | 0 | 0.9 | 0 | 11.9 |
| *19 | Black | 0.03 | 110 | −0.2 | 1.87 | 50 | 0.64 | 7 | 4 | 0 | 0.9 | 0 | 11.9 |
| *20 | Black | 0.05 | 105 | 0.5 | 1.22 | 55 | 0.19 | 5 | 2 | 0 | 0 | 0 | 7 |
| *21 | White | 0.01 | 24 | −1.1 | 0.35 | 36 | 0.25 | 0 | 0 | 0 | 0 | 0 | 0 |
| *22 | Black | 0.02 | 108 | 0.1 | 1.15 | 53 | 0.5 | 7 | 4 | 0 | 0.9 | 0 | 11.9 |

TABLE 2

| Sample No. | Thermal expansion coefficient $1/K \times 10^{-6}$ | Total reflection coefficient % | Brightness L* | Chromaticness b* | Processing method | Grain size of diamond abrasive μm | Polishing liquid | Buffing | Porosity vol. % | Difference in vertical positions among capillaries μm | Laser beam transmitted through ceramic member | Laser beam transmitted through capillary array |
|---|---|---|---|---|---|---|---|---|---|---|---|---|
| 1 | 0.1 | 7 | 34 | 6 | Lapping | Maximum 3 | Water | Not performed | 0.03 | 30 | Not observed | Detected |
| 2 | 0.3 | 7 | 35 | 5.5 | Lapping | Maximum 1 | Lubricant | Not performed | 0.04 | 20 | Not observed | Detected |
| 3 | 0.1 | 6 | 30 | 5 | Lapping | Maximum 1 | Lubricant | Not performed | 0.05 | 20 | Not observed | Detected |
| 4 | 0.4 | 6 | 30 | 4.1 | Lapping | Maximum 1 | Lubricant | Not performed | 0.05 | 20 | Not observed | Detected |
| 5 | 0.5 | 5 | 27 | 3.6 | Lapping | Maximum 0.5 | Lubricant | Performed | 0.03 | 10 | Not observed | Detected |
| 6 | 0.5 | 4 | 25 | 2.4 | Lapping | Maximum 0.5 | Lubricant | Performed | 0.03 | 10 | Not observed | Detected |
| 7 | 0.2 | 5 | 26 | −1.7 | Lapping | Maximum 0.5 | Lubricant | Performed | 0.03 | 10 | Not observed | Detected |
| 8 | 0.6 | 5 | 27 | 4.2 | Lapping | Maximum 0.5 | Lubricant | Performed | 0.04 | 10 | Not observed | Detected |
| 9 | 0.6 | 5 | 24 | 5 | Lapping | Maximum 0.5 | Lubricant | Performed | 0.03 | 10 | Not observed | Detected |
| 10 | 0.6 | 5 | 29 | −0.2 | Lapping | Maximum 0.5 | Lubricant | Performed | 0.06 | 10 | Not observed | Detected |
| 11 | 0.3 | 8 | 32 | 5.4 | Lapping | Maximum 1 | Water | Performed | 0.04 | 20 | Not observed | Detected |
| 12 | 0.7 | 5 | 25 | 3.8 | Lapping | Maximum 3 | Lubricant | Not performed | 0.06 | 30 | Not observed | Detected |
| 13 | 0.8 | 5 | 24 | 0.1 | Lapping | Maximum 3 | Water | Not performed | 0.06 | 30 | Not observed | Detected |
| 14 | 0.2 | 5 | 26 | −1.7 | Lapping | Maximum 3 | Water | Not performed | 0.02 | 40 | Not observed | Detected |
| 15 | 0.2 | 5 | 26 | −1.7 | Lapping | Average 3 | Water | Not performed | 0.03 | 40 | Not observed | Detected |
| 16 | 0.2 | 5 | 26 | −1.7 | Lapping | Average 3 | Water | Not performed | 0.04 | 40 | Not observed | Detected |
| 17 | 0.2 | 5 | 26 | −1.7 | Lapping | Maximum 0.3 | Lubricant | Performed | 0.03 | 0 | Not observed | Detected |
| 18 | 0.2 | 5 | 26 | −1.7 | Lapping | Maximum 0.5 | Lubricant | Performed | 0.03 | 50 | Not observed | Detected |
| *19 | 0.2 | 6 | 26 | −1.7 | Not performed | — | — | — | 0.03 | 80 | Not observed | Not transmitted |
| *20 | 0.1 | 7 | 34 | 6 | Flat surface polishing | — | — | — | 0.03 | 100 | Not observed | Not transmitted |
| *21 | 0 | 40 | 94 | −0.2 | Lapping | Maximum 0.3 | Lubricant | Performed | 0.03 | 20 | Observed | Could not be measured |
| *22 | 0.2 | 5 | 26 | −1.7 | Flat surface polishing | — | — | — | 0.03 | 80 | Not observed | Not transmitted |

As shown in Tables 1 and 2, all of Sample Nos. 1 to 18 according to embodiments of the present invention were black, had a flatness of not more than 0.02 mm, a mean spacing of waviness motifs (AW) of not more than 100 μm, and a difference in vertical positions among capillaries of not more than 50 μm. Furthermore, in all these samples, a laser beam transmitted through a support for capillaries was "not observed", and a laser beam was transmitted through a capillary array. These samples had a thermal expansion coefficient of not less than $0.1 \times 10^{-6}$/K and not more than $0.8 \times 10^{-6}$/K, a porosity in the range of 0.03% to 0.06% by volume, a total reflection coefficient in the range of 4% to 7%, a brightness L* in the range of 24 to 35, and a chromaticness b* of not more then 6.

Sample Nos. 1 to 13, and 17 which had an AW of not more than 50 μm, had a small difference in vertical positions among capillaries in the range of 10 to 30 μm. In contrast, Sample Nos. 14 to 16, and 18, which had an AW in the range of 55 to 100 μm, had a somewhat large difference in vertical positions among capillaries of 40 μm.

Sample Nos. 2 to 11 and Sample No. 17, which had a skewness (Rsk) of not more than zero, had a particularly small difference in vertical positions among capillaries in the range of 0 to 20 μm. Among these samples, Sample Nos. 5 to 10 and Sample No. 17, which had a $W_{EM}$ of not more than 1 μm, had the smallest difference in vertical positions among capillaries of 0 or 10 μm. Thus, waviness of capillaries could be suppressed.

Although not shown in Table 1, Sample Nos. 5 to 11 and Sample Nos. 17 and 18, which had a valley level of not more than 45%, were prepared by performing buffing. These samples had a difference in vertical positions among capillaries of not more than 10 μm, and thus, waviness of capillaries could be suppressed.

Samples that were out of the range of the present invention were prepared as in the above examples except for the conditions described below. The measurements were performed as in the above examples, and the samples were evaluated in the same manner. In Sample No. 19, polishing of the flat surface area was not performed. In Sample Nos. 20 and 22, a ceramic sintered body was polished with a diamond grinding stone rotating at a high speed, thus preparing a support for capillaries. In Sample No. 21, the support for capillaries did not contain a blackening agent.

As a result, in Sample Nos. 19, 20, and 22, a laser beam was not transmitted through the capillary array. In Sample No. 21, a laser beam was scattered, and whether or not the laser beam was correctly transmitted could not be confirmed. In Sample Nos. 20 and 21, although the values of the arithmetic mean roughness (Ra), which represents the surface roughness, were small, a laser beam was not transmitted through the capillary array. In contrast, although Sample Nos. 3, 4, and the like had a large arithmetic mean roughness Ra, satisfactory results were obtained because the flatness and the mean spacing of waviness motifs AW of these samples were within the range of the present invention. This result shows that the possibility of transmission of a laser beam does not significantly depend on the surface roughness. The ratios A/B of Sample Nos. 19 to 22 were not more than 0.5. Cracks were not observed in Sample Nos. 19, 21, and 22, but microcracks were observed on an end face of the support for capillaries used in Sample No. 20.

What is claimed is:

1. A support for capillaries, comprising:
    a ceramic member having a flat surface area on which the capillaries are to be aligned;
    wherein the flat surface area has a flatness of not more than 0.02mm and has a mean spacing of waviness motifs (AW) of not more than 100 μm;
    wherein the ceramic member comprises:
    a primary component made of a cordierite;
    Fe having an amount of not less than 5% by mass in terms of $Fe_2O_3$; and
    one or more elements selected from a group consisting of Ni, Co, Mn and Cr, in a amount of elements of not more than 5% and not including 0% by mass in terms of NiO, CoO, $MnO_2$ or $Cr_2O_3$, respectively;
    wherein a total amount of both Fe and the elements is not more than 15% by mass in terms of $Fe_2O_3$, NiO, CoO, $MnO_2$ or $Cr_2O_3$, respectively;
    wherein the ceramic member has the thermal expansion coefficient of not less than $0.1 \times 10^{-6}$/K and not more than $0.6 \times 10^{-6}$/K at a range from 20° C. to 60° C.

2. The support according to claim 1, wherein the flat surface area has a skewness (Rsk) of not more than 0.

3. The support according to claim 1, wherein the flat surface area has a maximum height of a rolling circle waviness profile ($W_{EM}$) of not more than 1μm.

4. The support according to claim 1, wherein the flat surface area has the valley level of not more than 45%, the valley level being shown by a following formula;

$$\text{Valley level} = \left[\left(\sum_{k=1}^{n} L_k\right)/L\right] \times 100\%$$

wherein assuming a hypothetical horizontal straight line crossing a concavo-convex shaped curve line obtained by linearly measuring a surface shape of the flat surface area along a direction and by drawing the surface shape on a basis of the measurement, the straight line being positioned so that a total of first areas surrounded by the straight line and concave portions of the curve line and a total of second areas surrounded by the straight line and convex portions of the curve line are substantially equal, $L_K$ is an each length of the straight line corresponding to each of the first areas, and L is a total length of the straight line.

5. The support according to claim 1, wherein a brightness L* noted by L*a*b* method of the ceramic member is not more than 30, and a total reflection ratio to light having a wave length from 350nm to 750nm of the ceramic member is not more than 7%.

6. The support according to claim 1, wherein an absolute value of a chromaticness b* noted by L*a*b* method of the ceramic member is not more than 5.

7. The support according to claim 1, wherein each of the mean spacings of waviness motifs of the flat surface area in both the alignment direction of the capillaries and the perpendicular direction to the alignment direction are not more than 100μm.

8. A case for constraining capillaries comprises:
    the support for capillaries according to claim 1
    side walls perpendicular to the flat surface area, constraining the capillaries;
    wherein a corner at a boundary between the flat surface area and the side walls has a curvature radius of not more than a curvature radius of the capillaries.

9. A measurement device comprising:

the support according to claim 1;

a plurality of capillaries arranged on a flat surface area of the support and having a measurement sample placed inside thereof;

a light emitting section to emit a measurement light to the measurement sample inside of the capillaries;

a detector to detect at least one of a transmitted light of the measurement sample and a fluorescence emitted from the measurement sample; and a measurement section to measure information detected by the detector and to output information measured in the measurement sample.

10. A measurement method comprising:

supplying a medium containing a measurement sample inside of a plurality of capillaries arranged on a flat surface area of the support according to claim 1;

emitting a measurement light to the measurement sample inside of the capillaries;

detecting at least either one of a transmitted light of the measurement sample and a fluorescence emitted by the measurement sample;

measuring information detected by a detector; and outputting information measured in the measurement sample.

* * * * *